(12) United States Patent
Van Tricht et al.

(10) Patent No.: US 10,345,259 B2
(45) Date of Patent: Jul. 9, 2019

(54) METHOD FOR QUANTIFICATION OF VIRUS PARTICLES USING CAPILLARY ZONE ELECTROPHORESIS

(71) Applicant: Janssen Vaccines & Prevention B.V., Leiden (NL)

(72) Inventors: Ewoud Van Tricht, Utrecht (NL); Lars Johannes Geurink, Leiden (NL); Catharina Elise Sänger-Van De Griend, Baarn (NL)

(73) Assignee: Janssen Vaccines & Prevention B.V., Leiden (NL)

(*) Notice: Subject to any disclaimer, the term of this patent is extended or adjusted under 35 U.S.C. 154(b) by 45 days.

(21) Appl. No.: 15/552,069

(22) PCT Filed: Feb. 18, 2016

(86) PCT No.: PCT/EP2016/053405
§ 371 (c)(1),
(2) Date: Aug. 18, 2017

(87) PCT Pub. No.: WO2016/131895
PCT Pub. Date: Aug. 25, 2016

(65) Prior Publication Data
US 2018/0011056 A1 Jan. 11, 2018

(30) Foreign Application Priority Data
Feb. 19, 2015 (EP) .................................. 15155743

(51) Int. Cl.
*G01N 27/447* (2006.01)
*C12Q 1/70* (2006.01)
*C12Q 1/04* (2006.01)

(52) U.S. Cl.
CPC ......... *G01N 27/44747* (2013.01); *C12Q 1/04* (2013.01); *C12Q 1/70* (2013.01);
(Continued)

(58) Field of Classification Search
None
See application file for complete search history.

(56) References Cited

U.S. PATENT DOCUMENTS 4,639,421 A * 1/1987 Sage, Jr. .................. C12Q 1/04
435/34
5,723,031 A 3/1998 Duerr et al.
(Continued)

OTHER PUBLICATIONS

Virtanen et al. Analytica Chimica Acta, 372 (1998) 231-239. (Year: 1998).*
(Continued)

*Primary Examiner* — Elis S Mekhlin
(74) *Attorney, Agent, or Firm* — Panitch Schwarze Belisario & Nadel LLP (57) ABSTRACT

The present invention provides a method for the quantification of virus particles in a biological sample, comprising the steps of: (a) introducing said biological sample comprising virus particles into a capillary tube containing a buffer solution; (b) applying an electrical field to said capillary tube of sufficient voltage to allow for the separation of the virus particles from additional constituents in said sample, to obtain electrophoretical fractions; (c) generating an electropherogram associated with the electrophoretical fractions; and (d) determining the concentration of virus particles in said sample by comparing the electropherogram with an electropherogram generated from a reference sample containing a known concentration of said virus particles.

17 Claims, 3 Drawing Sheets

(52) U.S. Cl.
CPC . *G01N 27/44756* (2013.01); *G01N 27/44791* (2013.01); *C12Q 2565/125* (2013.01)

(56) References Cited

U.S. PATENT DOCUMENTS

| | | | | |
|---|---|---|---|---|
| 5,993,626 A * | 11/1999 | Landers | ............... | G01N 27/447 204/451 |
| 2011/0165578 A1 * | 7/2011 | Verthelyi | ................. | C12Q 1/48 435/6.12 |
| 2013/0115382 A1 * | 5/2013 | Chiari | ................... | B01L 3/5027 427/535 |

OTHER PUBLICATIONS

Southern et al., Nucleic Acids Research, 1994, vol. 22, No. 8, 1368-1373. (Year: 1994).*

Int'l Search Report dated Apr. 8, 2016 in Int'l Application No. PCT/EP2016/053405.

Written Opinion dated Apr. 8, 2016 in Int'l Application No. PCT/EP2016/053405.

Mironov et al, "Viral Quantitative Capillary Electrophoresis for Counting Intact Viruses," Analytical Chemistry, vol. 83, pp. 5431-5435 (2011).

Azizi et al, "Viral Quantitative Capillary Electrophoresis for Counting and Quality Control of RNA Viruses," Analytical Chemistry, vol. 84, pp. 9585-9591 (2012).

Mathis et al, "Separation of Rotavirus Double-Layered Particles and Triple-Layered Particles by Capillary Zone Electrophoresis," Journal of Virological Methods, vol. 169, pp. 13-21 (2010).

Mann et al., "Capillary Zone Electrophoresis of a Recombinant Adenovirus", Journal of Chromatography A, vol. 895, pp. 329-337, 2000.

* cited by examiner

METHOD FOR QUANTIFICATION OF VIRUS PARTICLES USING CAPILLARY ZONE ELECTROPHORESIS

CROSS-REFERENCE TO RELATED APPLICATION

This application is a Section 371 of International Application No. PCT/EP2016/053405, filed Feb. 18, 2016, which was published in the English language on Aug. 25, 2016, under International Publication No. WO 2016/131895 A1, and the disclosure of which is incorporated herein by reference.

FIELD OF THE INVENTION

The present invention is directed to the analysis of biological samples in general, and more specifically to the quantitative analysis of biological samples utilizing capillary electrophoretic techniques. The invention in particular is directed to the quantitative analysis of biological samples containing adenovirus.

BACKGROUND OF THE INVENTION

Viruses, in particular adenoviruses, are potentially useful vectors for vaccination and/or gene therapy. Recombinant adenoviruses are a preferred class of viral vectors for use in vaccination or gene therapy. Robust and high yield processes for large scale manufacturing are needed to support the world with sufficient amounts of (recombinant) vaccines to combat infectious diseases. In support of commercial scale production reliable analytical methods are required to monitor the quantities of (adeno)viruses throughout the manufacturing process (from upstream processing to downstream processing) to ensure the safety, efficacy and quality of (adeno)virus-based vaccines/therapies.

In addition, during process development and for production of adenovirus-based clinical trial material, samples are analysed in order to either monitor or control the production process and the safety of the product. One of the analyses typically performed on such samples is the determination of the total concentration of intact adenovirus particles. Current methods with limited suitability for this purpose are quantitative polymerase chain reaction (qPCR) and anion exchange chromatography (AEX-HPLC). qPCR is based on DNA amplification of a region specific for the adenovirus and fluorescence detection of the formed amplicon. Quantitative PCR is an expensive (cost price of chemicals) and laborious technique. The total time from sampling to result reporting can be up to three days, since numerous replicates are required for the results to have acceptable precision. An additional drawback is that qPCR determines the concentration of adenovirus particles indirectly by determining the DNA content of the particles instead of determining the intact particles themselves.

AEX-HPLC with UV detection makes use of a charge-based separation of intact adenoviruses from sample matrix components. Quantification is performed by external calibration using an adenovirus reference standard. The AEX-HPLC method suffers from adsorption, carry-over and recovery issues for samples containing cell lysate or high salt concentrations, and is therefore not suitable to determine the concentration of adenoviruses accurately and precisely throughout the entire production process.

There thus is a need for an improved method for the quantification of (adeno)viruses. In particular, in order to support process development for (adeno)virus based vaccines, it would be useful to have one single method that allows for direct quantification of (adeno)virus particles throughout the process with high accuracy and precision and with a short time to result, without the drawbacks of for example adsorption, carry-over and/or poor recovery.

SUMMARY OF THE INVENTION

The present invention provides a novel method for quantification of virus particles, in particular adenovirus particles, in a biological sample, said method comprising the steps of:
  a) introducing said biological sample comprising virus particles into a capillary tube containing a buffer solution;
  b) applying an electrical field to said capillary tube of sufficient voltage to allow for the separation of the virus particles from additional constituents in said sample to obtain electrophoretical fractions;
  c) generating an electropherogram associated with said electrophoretical fractions; and
  d) determining the concentration of virus particles in said biological sample by comparing the electropherogram with an electropherogram generated from a reference sample containing a known concentration of said virus particles, preferably by comparing the peak area of the electophoretical fraction corresponding to the virus particles with the peak area of a reference sample, comprising containing a defined concentration of virus particles.

The method according to the invention has been shown to be a robust, accurate, reliable and fast method for the quantification of (adeno)virus particles in all types of biological samples derived from both upstream and downstream development and manufacturing processes. Samples with highly different matrices can be analysed in long sequences without the need for prior processing, and/or for example the drawbacks of adsorption, carry-over or poor recovery. The total analysis time from process sampling to reported result can be less than 2 hours. The method according to the invention requires no special treatment for detection. The virus particles are detected directly and staining or labelling of the virus particles is not needed.

DETAILED DESCRIPTION OF THE INVENTION

The present invention provides a novel simple and reliable method for quantification of virus particles, in particular adenovirus particles, in a biological sample, said method comprising:

a) a) introducing said biological sample comprising virus particles into a capillary tube containing a buffer solution;

b) b) applying an electrical field to said capillary tube of sufficient voltage to allow for the separation of the virus particles from additional constituents in said sample to obtain electrophoretical fractions;

c) c) generating an electropherogram associated with said electrophoretical fractions; and d) determining the concentration of virus particles in said biological sample by comparing the electropherogram with an electropherogram generated from a reference sample containing a known concentration of said virus particles.

In certain embodiments, the concentration of virus particles, in particular the adenovirus particles, in said biological sample is determined by comparing the peak area of the electophoretical fraction corresponding to the (adeno)virus particles with the peak area of a reference sample containing a known concentration of said (adeno)virus particles.

The method of the invention is based on capillary electrophoresis ("CE"), in particular capillary zonal electrophoresis ("CZE"). CZE is a technique which permits rapid and efficient separations of charged substances. In general, CZE involves introduction of a sample into a capillary tube, i.e. a tube having an internal diameter of from about 2 to about 200 microns and the application of an electric field to the tube. The electric potential of the field both pulls the sample through the tube and separates it into its constituent parts. Thus, each of the sample constituents has its own individual electrophoretic mobility; those having greater mobility travel through the capillary tube faster than those with slower mobility. As a result, the constituents of the sample are resolved into discrete zones in the capillary tube during their migration through the tube. An on-capillary or on-line detector can be used to continuously monitor the separation and provide data as to the various constituents based upon the discrete zones, i.e. the discrete electrophoretical fractions. The peak area of the virus correlates with the quantity of the virus and is suitable for the direct quantification of the virus particle concentration.

In the research that led to the present invention it has been found that CZE can be used to accurately quantify the concentration of virus particles, in particular adenovirus particles, in biological samples derived from different stages throughout the manufacturing process, i.e. from the start of the process wherein the samples may contain cell lysate, cell debri and high concentrations, towards the end of the manufacturing process, wherein the samples are purified samples such as drug substances and drug product. The determination is based on the direct detection of intact particles, not on the indirect determination by measuring particle components such as DNA or RNA. As shown in the Examples below, the present invention demonstrates that CZE provides a high level of reproducibility and robustness over a range of assay conditions. Thus, the present invention allows for standardization and optimization of commercial production of virus based vaccines and/or gene therapies, in particular adenovirus based vaccines and/or gene therapies.

According to the invention, the virus containing preparation can be brought on the capillary and the quantity of (adeno)virus particles in the preparation can be calculated from the specific peak areas. Samples with highly different matrices can be analysed in long sequences without the drawbacks of the methods of the prior art, such as for example adsorption, carry-over or poor recovery. With the method of the invention, it is thus possible to measure several complex samples without the drawbacks that are seen with the methods of the prior art. The actual run time of individual samples can be less than 5 minutes and the total analysis time from process sampling to reported result can be less than 2 hours. The invention thus provides a fast and accurate means for determining the virus concentration during the manufacturing process of virus-based vaccines, in particular adenovirus-based vaccines, thereby overcoming most of the problems associated with the methods known in the art.

According to the invention, the buffer is carefully designed to enhance detectability and recovery of the virus particles and to reduce aggregation or adsorption of components of the biological sample comprising the virus particles.

In certain embodiments, the buffer solution comprises tris(hydroxymethyl)aminomethane in a concentration of between about 100 and 500 mM and tricine in a concentration of between 100 and 500 mM, and has a pH of between 7.3 and 8.9.

In certain embodiments, the buffer solution comprises tris(hydroxymethyl)aminomethane in a concentration of between about 100 and 300 mM and tricine in a concentration of between 100 and 412.5 mM, and has a pH of between 7.5 and 8.5.

In certain embodiments, the buffer solution comprises tris(hydroxymethyl)aminomethane in a concentration of between about 100 and 150 mM and tricine in a concentration of between 300 and 350 mM; and has a pH of between 7.5 and 7.8.

In certain preferred embodiments, the buffer solution comprises tris(hydroxymethyl)aminomethane in a concentration of about 125 mM and tricine in a concentration of about 337.5 mM, and has a pH of about 7.7.

According to the invention, the capillary tube is treated such that adsorption of components of the biological sample comprising the (adeno)virus particles is prevented or greatly reduced.

In certain embodiments, the capillary tube is flushed by reversed flushing with phosphoric acid in a concentration of between about 5 and 20 mM prior to a flush with the buffer solution.

In certain preferred embodiments, the capillary tube is flushed by reversed flushing with 10 mM phosphoric acid prior to a flush with the buffer solution.

In certain embodiments, the buffer solution further comprises a surfactant to reduce virus particle aggregation or capillary wall adsorption.

In certain embodiments, the buffer solution further comprises a neutral surfactant to reduce virus particle aggregation or capillary wall adsorption.

In certain preferred embodiments, the buffer solution further comprises polysorbate 20 in a concentration of between 0.02 and 0.3% v/v, preferably in a concentration of between 0.1 and 0.3% v/v, more preferably a concentration of 0.2% v/v.

In certain embodiments, the separation of the virus particles is performed at between 10 and 40° C.

In certain preferred embodiments, the separation of the viral particles is performed at 15° C.

In certain embodiments, the method is conducted using neutral coated capillary tubes.

In certain preferred embodiments, the method is conducted in a polyvinyl alcohol (PVA) or a fluorocarbon polymer (e.g. µSIL-FC) coated capillary tube.

In some embodiments, the method is conducted using a capillary tube ranging between 30 and 100 cm in total length and between 8 and 100 cm effective length (length from inlet to detector). In some embodiments, CZE is conducted using a capillary of 30 cm in total length and 8.5 cm in effective length. In some embodiments, the capillary tube has 10-200 µm, preferably a 50 µm, inside diameter.

According to the invention, an electrical field is applied to said capillary tube of sufficient voltage to allow for the separation of the virus particles. This separation is typically attained by the use of high voltages, typically 5,000 to 30,000 volts, preferably 10,000 to 30,000 volts, which can generate electroosmotic and electrophoretic flow of the buffer solution and ionic species within the capillary tube. The field strength applied for separation is typically between 30 and 100 kV/m and preferably 70-80 kV/m.

According to the invention, the biological sample can be any (aqueous) liquid sample matrix containing organic or inorganic components, protein moieties, nucleotides or other viruses, such as samples from upstream or downstream process development and manufacturing. In certain embodiments of the present invention, the biological sample is a sample derived from cell culture, i.e. from an upstream process. Said biological sample thus may contain other constituents, such as cell lysate, cell debri, and/or high salt concentrations. In addition, also during downstream processing, it is very important to monitor virus recovery. Thus, in other embodiments, the biological sample may be derived from a downstream process, i.e. may be a high salt sample or purified sample, such as for example in the case of drug substance and drug product. It is an advantage of the method according to the invention that the method can be used for all samples obtained throughout the manufacturing process, even samples comprising cell debri, nucleotides, proteins or high salt concentrations. In contrast, the quantification method used in the art, such as AEX-HPLC, is not suitable for samples containing cells and high concentrations of salt. The method of the present invention now enables one of skill in the art to quantify virus particles that are present in a biological sample, even if the biological sample comprises other constituents, such as cells, cell debri, nucleotides, proteins etc., in a very robust, rapid and accurate way.

The process of capillary zonal electrophoresis can be carried out in any apparatus in which the suitable electrophoretic field can be generated and in which the resulting electrophoretical fractions can be detected and/or in which the capillary tube can be flushed backwards. The capillary tube typically is filled with buffer solution and sample injection is performed by a hydrodynamic injection method, wherein a pressure drop (e.g. 5 kPa during 5 s) is applied along the capillary either by high pressure at the injection side, vacuum at the detector side, or hydrostatic pressure using gravity. The electrical field is applied by means of a high voltage power supply. The virus particles are detected directly and staining or labelling of the virus particles are not needed. In certain embodiments, a detector, for example a detector comprising of an ultraviolet emitter (deuterium lamp) and monochromator to select the desired wavelength, as well as a photodetector to detect the ultraviolet light that has passed through the sample, is located at the end of the capillary which is opposite to the injection site. The signal preferably is detected at a wavelength of between 200-400 nm. In some embodiments the wavelength is 214 nm. Preferably, the signal detected is proportional to the quantity of the virus particles present in the sample. A plot of the detector response versus the migration time is called an electropherogram. A computer connected to the detector allows data acquisition and interpretation of the electropherogram.

According to the invention, the concentration of virus particles in the biological sample is determined by comparing the electropherogram with an electropherogram generated from a reference sample containing a known concentration of said virus particles. In certain embodiments of the method according to the invention, such quantitative analysis of the biological sample is performed by comparing the peak areas of the electrophoretical fractions corresponding to the (adeno)virus particles with the peak area of a reference sample, comprising a defined concentration of (adeno)virus particles. The reference sample can for example be used to prepare a standard curve of the peak area versus the (adeno)virus particle concentration. Quantification of the (adeno)virus particles present in the biological sample is then subsequently carried out based on the standard curve prepared for the reference sample.

The method of the invention is suitable for quantification of different types of virus particles in a biological sample, such as for example polioviruses.

In certain embodiments, the virus particles are recombinant adenovirus particles. Preferably, the adenoviruses are deficient in at least one essential gene function of the E1 region, e.g., the E1a region and/or the E1b region, of the adenoviral genome that is required for viral replication. Such recombinant adenoviruses are usually deficient in at least the E1 region, and are propagated in complementing cells providing the E1-region, such as 293 cells, or E1-immortalized retina cells such as PER.C6 cells (see for instance U.S. Pat. No. 5,994,128). In certain embodiments, the adenovirus particles are adenovirus 5 particles, adenovirus 26 particles or adenovirus 35 particles.

The invention is further illustrated in the following non-limiting Examples.

EXAMPLES

Example 1

As described above, Mann et al. (Journal of Chromatography A, 895:329-337, 2000) have established a capillary zone electrophoresis (CZE) method for the analysis of recombinant adenovirus 5. The use of CZE for the quantification of adenovirus, however, as well as the ability of CZE to support vaccine process development, was not demonstrated nor suggested. In the research that led to the invention it was shown that that this method is, due to adsorption and/or aggregation issues, not suitable for multiple injections nor for samples with complex matrices such as harvest samples. Dürr et al. (U.S. Pat. No. 5,723,031) described a general capillary electrophoresis method for the analytical separation of viruses in body liquids. This method needs extensive sample purification with a CsCl density gradient to isolate the virus particles. Additionally, a DNA/RNA-binding reagent needs to be added to the separation buffer for staining the virus particles prior to detection. It was further shown that separation buffer with 25 mM Tris and 192 mM glycine pH 8.5 in combination with a standard fused silica capillary as described was not suitable for the determination of the concentration of adenovirus particles. No peaks were observed, which could be due to both unfavourable migration as well as adsorption of virus particles to the capillary wall. The separation buffer of with additional SDS was not tested, as SDS degrade adenovirus particles. Two papers from the group of Berezovski (Mironov et al, Analytical Chemistry, 83: 5431-5435, 2011 and Azizi et al, Analytical Chemistry, 84, 9585-9591, 2012) have described the determination of the concentration of viruses by capillary electrophoresis with fluorescence detection in an indirect way. Instead of determining the virus particles, the DNA and/or RNA fraction from host protein and virus is determined. An intercalating dye is needed for fluorescence detection. Mathis et al. (Journal of Virological Methods 169, 13-21, 2010) furthermore have described a CE method for the separation and concentration determination analysis of CsCl purified double and triple layered rotavirus particles. The separation buffer used was a 50 mM phosphate buffer pH 8.0 with 10 mM putrescine added as EOF modifier. SDS was added to CsCl purified samples to prevent adsorption and aggregation. In the research that led to the present invention, a phosphate buffer pH 8.0 with putrescine was tested for quantifying adenovirus particles. No virus particles were observed. Furthermore, adenovirus particles are not compatible with SDS, as the particles degrade.

According to the invention, a tris(hydroxymethyl)aminomethane-tricine buffer was carefully selected as separation buffer for the determination of the concentration of virus particles in a wide range of sample matrices. Tricine has a $pK_a$ of 8.15 and tris(hydroxymethyl)aminomethane (tris) has a $pK_a$ of 8.07. This means that the tris-tricine buffer contains both a buffering co-ion as well as a buffering counter-ion. The pH close to the $pK_a$s as well as the relative high concentration gives a strong buffering capacity. The use of zwitterions with low conductivity means that the high concentration results in a moderate current, so there will be no excessive Joule heating at normal electric field strengths. The high buffer concentration reduces virus particle aggregation. This was apparent by the disappearance of the typical spikes as mentioned by Azizi (Analytical Chemistry, 84, 9585-9591, 2012) and the normal peak shapes that were obtained for adenovirus particles. Furthermore, the high buffer concentration has a high sample stacking potential. This means that it is possible to inject large volumes of diluted sample as well as that the method will be less sensible to peak distortions and migration variability caused by sample matrix variability.

The tris(hydroxymethyl)aminomethane-tricine buffer was optimized in a full factorial design to obtain the best separation efficiency and signal-to-noise ratio for the adenovirus particles and to reduce the total run time. The tris (hydroxymethyl) was tested in a range of 100-300 mM, and tricine was tested between 100-412.5 mM. The data were evaluated based on resolution between adenovirus and matrix components, total run time, and signal-to-noise ratio. The best results, regarding sample criteria as described above, were 100-150 mM tris(hydroxymethyl)aminomethane and 300-350 mM tricine at pH 7.5-7.8.

Virus sample adsorption is a major issue for any separation technique. In CE, the sample only is in contact with the sample vial and the capillary. To reduce adsorption, a neutral coated capillary tube was used and surfactant was added to the separation buffer and the capillary conditioning was investigated in detail. SDS is not a suitable surfactant to add to the separation buffer, as adenovirus particles degrade in the presence of SDS. Polysorbate is a neutral surfactant. The use of a neutral surfactant has the additional advantage that it does not contribute to the total current in the system and the concentration can be varied with little risk of additional Joule heating and thus virus particle band broadening. Addition of polysorbate 20 to the separation buffer reduced adsorption and improved migration time and peak area repeatabilities. Polysorbate 20 was added to the run buffer in a concentration of 0.2% v/v, but was suitable in a range between 0.02 and 0.3% v/v. Adsorption was further reduced by optimized capillary conditioning. The best results were obtained by flushing 2 minutes with 10 mM phosphoric acid prior to a 2 minutes flush with the buffer solution. It proved to be crucial that this flushing is performed from outlet to inlet, that is, reversed flushing. Reducing the separation temperature to lower temperatures such as 15° C. further reduced aggregation and adsorption. According to the invention, it was shown that without these adsorption reducing measures, multiple injections from the same sample resulted in a decrease in peak area (and therefore adenovirus concentration). In average, it was possible to run up to 8 samples. With the combination of these adsorption preventing measures it was possible to run more than 400 injections on one capillary without losing peak area and none of those injections showed the typical aggregation peak spikes mentioned above.

Figure 2:
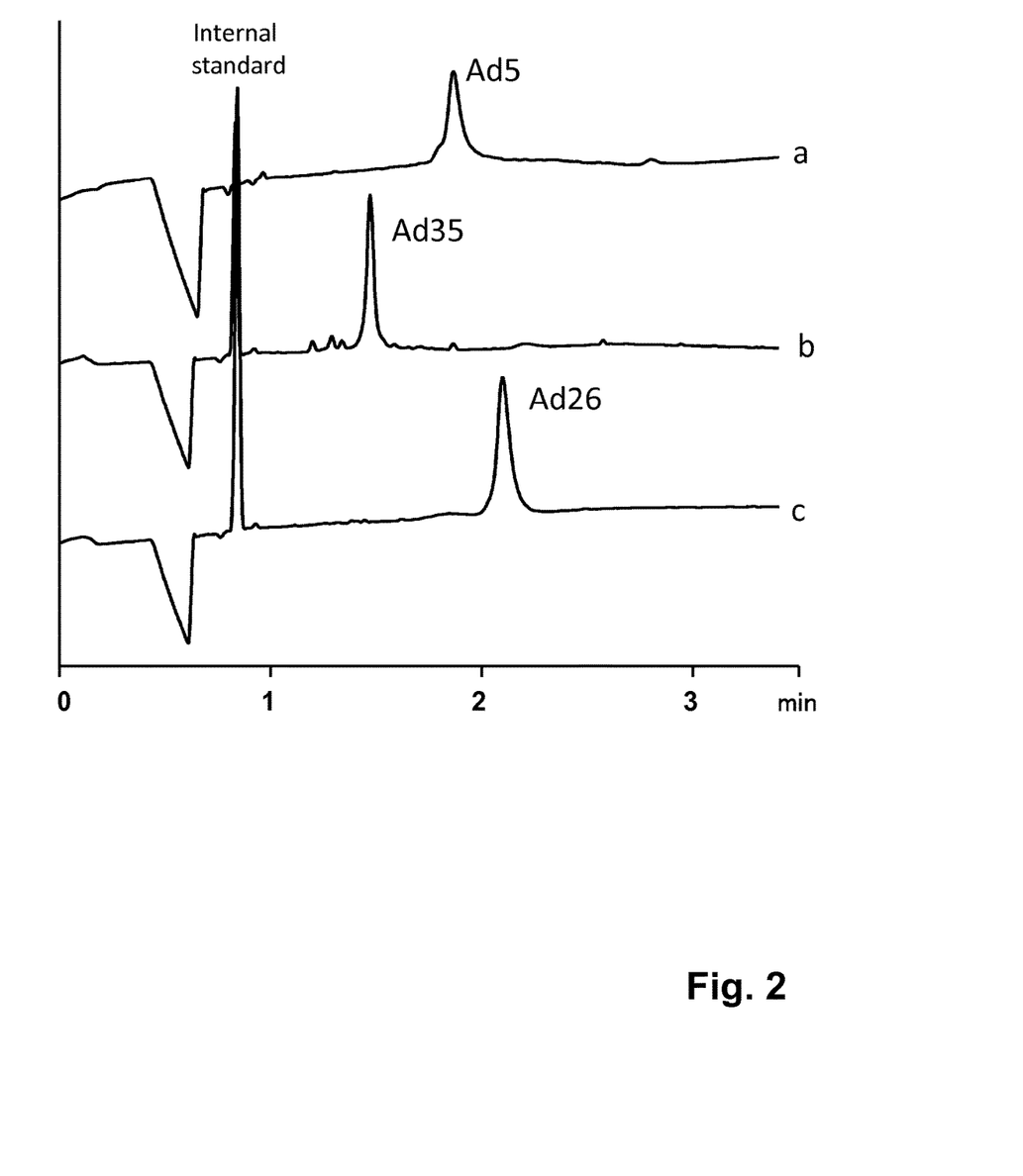
FIG. 2: Electropherograms of (a) Ad5, (b) Ad35, and (c) Ad26. Conditions: Buffer: 125 mM tris-338 mM tricine, pH 7.7, and 0.2% polysorbate-20 effective length of capillary: 8.5 cm, applied voltage: −25 kV. All samples were diluted to $1 \times 10^{11}$ vp/ml.

Analytical procedures typically should be validated for their intended use. ICH Q2 *Validation of Analytical procedures: text and methodology* gives guidance on the characteristics for consideration during the validation of analytical procedures. The intended use of the developed CZE method is categorized as a quantitative test (also called assay) of the virus particles in samples of drug substance or drug product. Assay procedures are intended to measure the analyte present in a given matrix. The developed CZE method was validated according ICH Q2. The following characteristics for assay procedures were assessed: accuracy, precision (repeatability and intermediate precision), specificity, linearity, and range (FIG. 2).

Repeatability expresses the precision under the same operating conditions over a short interval of time (ICH Q2). The repeatability was calculated for migration time and peak areas was determined based on the analysis of 6 independent preparations of adenovirus samples on 3 different days (n=6 on 3 days). The repeatability of the adenovirus peak area was, on each day, between 2.1 and 4.8% CV (coefficient of variation) and between 0.55 and 0.82% CV for the migration time.

The intermediate precision (intermediate precision expresses within-laboratories variations: different days, different analysts, different equipment, etc.) was also calculated based on the migration time and peak areas and is expressed as the total coefficient of variation. The intermediate precision was based on the analysis of 6 independent preparations of adenovirus samples on 3 different days (n=18) performed by 2 operators, 2 systems etc. The intermediate precision, over 3 days, of the adenovirus peak area was 7.8% CV and was 2.5% CV for the migration time.

The linearity of an analytical procedure is its ability (within a given range) to obtain test results which are directly proportional to the concentration (amount) of analyte in the sample. The linearity of adenovirus concentration and the absorption was measured on 3 different days based on 5 concentration levels and each concentration level was independently prepared 3 times (n=15 on 3 days). The linearity experiment showed that the concentration of adenovirus on each day was significant linear with a determination coefficient of $R^2>0.98$.

The accuracy of an analytical procedure expresses the closeness of agreement between the value which is accepted either as a conventional true value or an accepted reference value and the value found. The accuracy as recovery of the adenovirus concentration was determined in the same setup as the linearity (n=15 on 3 days). The only difference was that the samples were diluted in AEX elution buffer (AEX product matrix) instead of formulation buffer. The recovery was between 93% and 110% for all concentrations. No effect of the matrix compositions was observed. All data were significantly linear.

The range of an analytical procedure is the interval between the upper and lower concentration (amounts) of analyte in the sample (including these concentrations) for which it has been demonstrated that the analytical procedure has a suitable level of precision, accuracy and linearity. The range of the analytical method was determined to be $0.18 \times 10^{11}$ to $1.8 \times 10^{11}$ virus particle per ml. In this range accuracy, linearity and precision was demonstrated.

Figure 1:
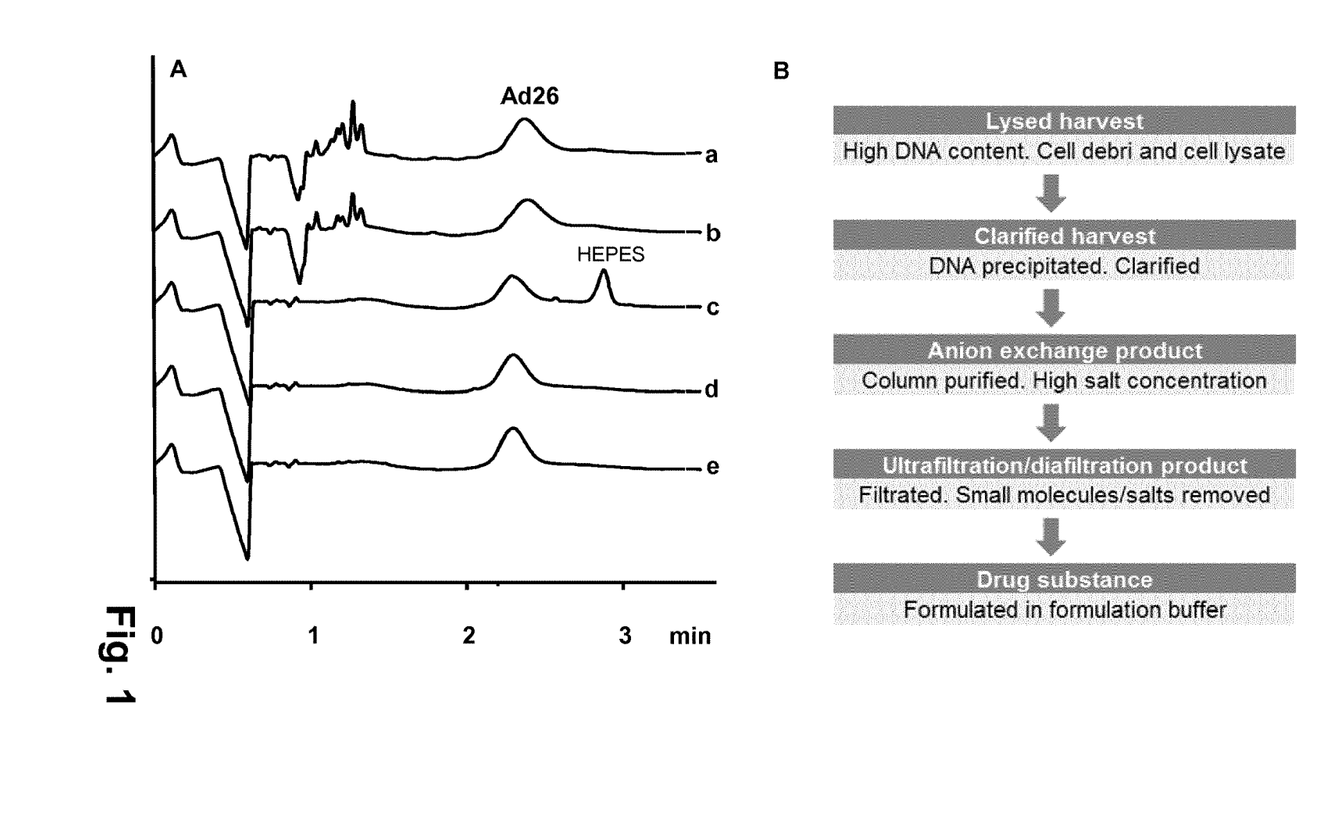
FIG. 1: A) Electropherograms of Ad26 (a) lysed harvest, (b) clarified harvest, (c) anion-exchange product, (d) diafiltration/ultrafiltration product, (e) drug substance, and (f) reference standard of adenovirus type 26. Lysed harvest, clarified harvest and anion exchange product were treated with benzonase. Conditions: Buffer: 125 mM tris-338 mM tricine, pH 7.7, and 0.2% polysorbate-20 effective length of capillary: 8.5 cm, applied voltage: −25 kV. All samples were diluted to $1 \times 10^{11}$ vp/ml. B) Flowchart of downstream process samples.

Specificity is the ability to assess unequivocally the analyte in the presence of components which may be expected to be present. Typically these might include impurities, degradants, matrix, etc. The specificity was demonstrated during the development of the method of the invention. Adenovirus type 35 could be separated from adenovirus type 26. None of the known (internal standard, HEPES) or unknown peaks interfered with either adenovirus type 26 or 35 (See FIG. 1A).

The CZE method according to the invention was applied for the analysis of a series of adenovirus type 26 process samples according to the process depicted in FIG. 1B. Prior to analysis, the lysed harvest, bulk clarified harvest, and anion exchange product samples were treated with benzonase (0.2 units benzonase per milliliter, 31 mM MgCl, incubation 1 hour at RT). As a reference sample (also calibration standard) adenovirus type 26 material was used with a known concentration.

The samples and the reference material were analysed according to the following conditions without additional sample preparation:
Capillary dimensions: 8.5 cm effective length, 50 µm inner diameter
Capillary coating: PVA coated
Buffer system: Tris(hydroxymethyl)aminomethane-Tricine-Polysorbate 20)
    Concentrations:
        Tris(hydroxymethyl)aminomethane: 125 mM
        Tricine: 337.5 mM
        Polysorbate 20: 0.2% v/v
Preconditioning of capillary
    Reversed flushing with 20 column volumes phosphoric acid 10 mM
    Reversed flushing with 20 column volumes separation buffer
Injection: Hydrodynamic injection (5 kPa for 5 s)
Separation conditions
    Temperature: 15° C.
    Voltage: 25 kV (Field strength 76 kV/m)
    Detection: 214 nm, spectral analysis for specificity (200-400 nm)
Run time:
    3.5 min per run when injected at short-end of capillary
A selection of the data obtained for the reference sample and the test samples is shown in FIG. 1A. The adenovirus peak is clearly separated from all other unknown and known peaks in all materials. The adenovirus fraction had the same migration time in all types of material (approx. 2.2 min). The AEX product sample (FIG. 1 trace C) clearly shows the HEPES peak originating from the AEX buffer. The calculated concentrations for the AEX product and formulated bulk are summarized in Table 2.

TABLE 2

Overview of calculated concentrations (in vp/ml) for lysed harvest, clarified harvest, anion-exchange product, diafiltration/ultrafiltration product, drug substance in comparison with the reference material

| Type of material | n | Calculated concentration (vp/ml) |
|---|---|---|
| Adenovirus type 26 lysed harvest | 6 | $5.4 \times 10^{11}$ |
| Adenovirus type 26 Bulk clarified harvest | 6 | $2.3 \times 10^{11}$ |
| Adenovirus type 26 anion-exchange product | 6 | $1.1 \times 10^{12}$ |
| Adenovirus type 26 diafiltration/ultrafiltration product | 6 | $3.4 \times 10^{11}$ |
| Adenovirus type 26 Drug substance | 6 | $3.4 \times 10^{11}$ |

Example 2

Figure 3:
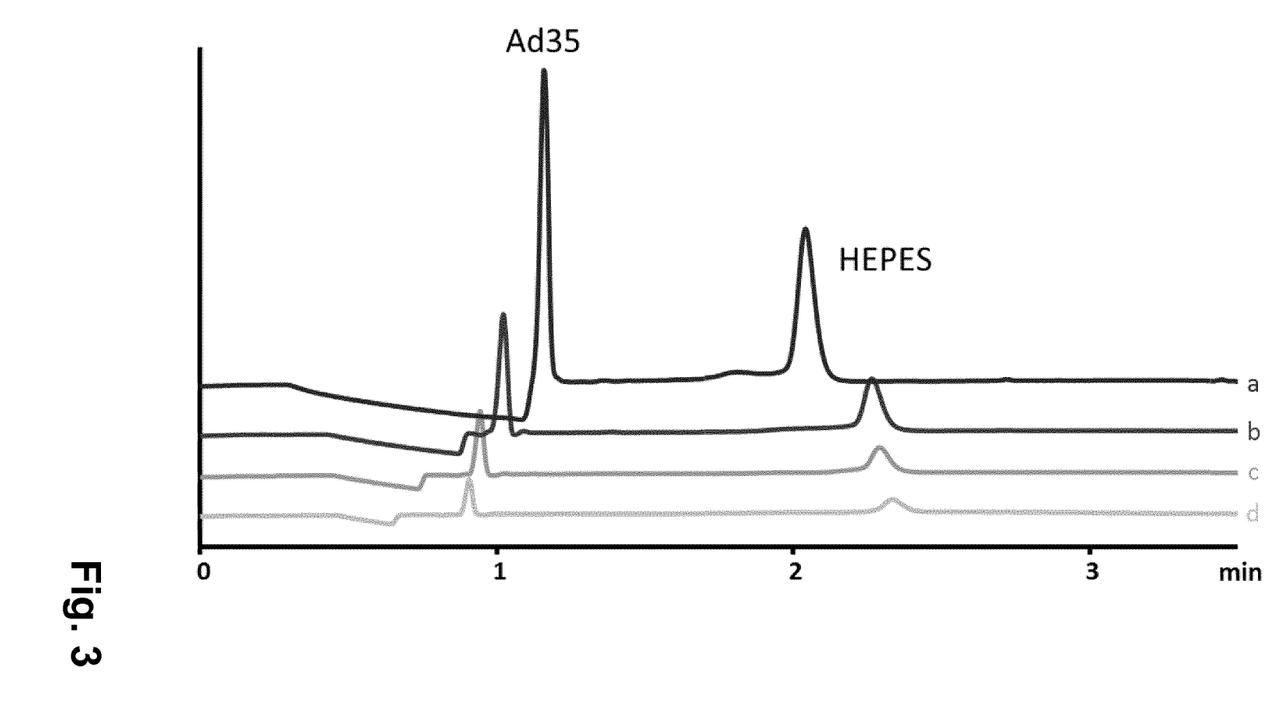
FIG. 3: Electropherograms of Ad35 anion-exchange product injected with 5 kPa during (a) 50 s, (b) 20 s, (c) 10 s, or (d) 5 s. Conditions: Buffer: 113 mM tris-338 mM tricine, pH 7.7, and 0.2% polysorbate-20, effective length of capillary: 8.5 cm, applied voltage: −25 kV. All samples were diluted to $1\times10^{11}$ vp/ml.

The composition of the separation buffer solution according to the invention allows larger injection volumes. In this way, better sensitivity can be achieved. In FIG. 3 an example of Ad35 anion exchange product is shown at different injection volumes (pressure×time). It was shown that with a 10× longer injection there was still separation of the adenovirus peak. At this level of injection volume the precision of respectively the adenovirus peak migration time and the corrected adenovirus peak areas are 2% RSD and 3% RSD. No difference in accuracy and capillary lifetime were observed between different injection volumes.

The invention claimed is:

1. A method for direct quantification of adenovirus particles in a biological sample, comprising:
    a) introducing the biological sample comprising virus particles into a capillary tube containing a buffer solution;
    b) applying an electrical field to the capillary tube of 10,000 to 30,000 Volts to allow for the separation of the adenovirus particles from additional constituents in the sample, to obtain electrophoretical fractions;
    c) generating an electropherogram associated with the electrophoretical fractions; and
    d) determining the concentration of the adenovirus particles in the sample by comparing the electropherogram with an electropherogram generated from a reference sample containing a known concentration of the adenovirus particles,
    wherein the buffer solution comprises tris(hydroxymethyl)aminomethane in a concentration of between about 100 and 500 mM and tricine in a concentration of between 100 and 500 mM, and has a pH of between 7.3 and 8.9, and wherein the capillary tube is flushed in reverse direction with a phosphoric acid solution before the capillary tube is flushed and filed with the buffer solution.

2. The method according to claim 1, wherein the buffer solution comprises tris(hydroxymethyl)aminomethane in a concentration of between about 100 and 300 mM and tricine in a concentration of between 100 and 412.5 mM, and has a pH of between 7.5 and 8.5.

3. The method according to claim 1, wherein the buffer comprises tris(hydroxymethyl)aminomethane in a concentration of between about 100 and 150 mM, and tricine in a concentration of between 300 and 350 mM and has a pH of between about 7.5 and 7.8.

4. The method according to claim 1, wherein the buffer solution further comprises polysorbate 20 in a concentration of between 0.1 and 0.3% v/v.

5. The method according to claim 1, wherein the capillary tube is a neutral coated capillary tube.

6. The method according to claim 5, wherein the capillary tube is coated with a polyvinyl alcohol (PVA) or a fluorocarbon polymer.

7. The method according to claim 1, wherein the phosphoric acid solution comprises 5 to 20 mM phosphoric acid.

8. The method according to claim 1, wherein the separation is performed at a temperature of about 15° C.

9. The method according to claim 1, wherein the adenovirus particles are recombinant adenovirus particles.

10. The method according to claim 1, wherein the adenovirus particles are adenovirus 5, adenovirus 26 or adenovirus 35 particles.

11. A method for direct quantification of adenovirus particles in a sample, comprising:
    a) introducing the sample into a neutral coated capillary tube containing a buffer solution;
    b) applying an electrical field to the neutral coated capillary tube at a voltage of 10,000 to 30,000 Volts to allow for the separation of the adenovirus particles from additional constituents in the sample, to thereby obtain electrophoretical fractions;
    c) generating an electropherogram associated with the electrophoretical fractions; and
    d) determining the concentration of the adenovirus particles in the sample by comparing the electropherogram with an electropherogram generated from a reference sample containing a known concentration of the adenovirus particles,
wherein,
    the buffer solution comprises 100-150 mM tris(hydroxymethyl)aminomethane, 300-350 mM tricine and 0.1-0.3% polysorbate, and has a pH of 7.5 to 7.8, and
    the capillary tube is flushed, in a direction from outlet to inlet of the capillary tube, with a phosphoric acid solution before the capillary tube is filed with the buffer solution.

12. The method according to claim 11, wherein the neutral coated capillary tube is coated with a polyvinyl alcohol (PVA).

13. The method according to claim 11, wherein the neutral coated capillary tube is coated with a fluorocarbon polymer.

14. The method according to claim 11, wherein the phosphoric acid solution comprises 5 to 20 mM phosphoric acid.

15. The method according to claim 11, wherein the separation is performed at a temperature of about 15° C.

16. The method according to claim 11, wherein the electrical field is applied to the neutral coated capillary tube at a voltage of 25,000 Volts.

17. The method according to claim 11, wherein the buffer solution comprises 125 mM tris(hydroxymethyl)aminomethane, 338 mM tricine and 0.2% polysorbate 20.

* * * * *